United States Patent [19]
Walling et al.

[11] Patent Number: 5,948,394
[45] Date of Patent: Sep. 7, 1999

[54] TRANSFER-RESISTANT LIP COMPOSITIONS

[75] Inventors: David William Walling, Parkton; Steven Michael Wujek; Felicia Levine, both of Bel Air; Debra Joy Coleman-Nally, Finksburg, all of Md.

[73] Assignee: The Procter & Gamble Company, Cincinnati, Ohio

[21] Appl. No.: 08/782,139

[22] Filed: Jan. 13, 1997

Related U.S. Application Data

[60] Provisional application No. 60/009,936, Jan. 16, 1996, and provisional application No. 60/015,487, Apr. 15, 1996.

[51] Int. Cl.$^6$ .......................... A61K 7/027; A61K 7/025
[52] U.S. Cl. .......................... 424/64; 424/63; 424/DIG. 5
[58] Field of Search .......................... 424/64, 63, DIG. 5

[56] References Cited

U.S. PATENT DOCUMENTS

| | | | |
|---|---|---|---|
| 5,288,482 | 2/1994 | Krzysik | 424/64 |
| 5,505,937 | 4/1996 | Castrogiovanni et al. | 424/64 |
| 5,650,139 | 7/1997 | Nojima | 424/64 |

FOREIGN PATENT DOCUMENTS

| | | |
|---|---|---|
| 0692238A1 | 7/1994 | European Pat. Off. . |
| 0706789A1 | 10/1994 | European Pat. Off. . |
| 0709083A2 | 10/1994 | European Pat. Off. . |
| 5-221829 | 8/1993 | Japan . |
| WO 95/11000 | 4/1995 | WIPO . |
| WO 96/19185 | 6/1996 | WIPO . |
| WO 96/40044 | 12/1996 | WIPO . |

OTHER PUBLICATIONS

CTFA Cosmetic Ingredient Handbook, p. 567, 1992.
CTFA Cosmetic Ingredient Handbook, pp. 572–575, 1992.
CTFA Cosmetic Ingredient Handbook, pp. 578–580, 1992.
CTFA Cosmetic Ingredient Handbook, pp. 587–592, 1992.

*Primary Examiner*—Jyothsna Venkat
*Attorney, Agent, or Firm*—Loretta J. Henderson; George W. Allen; John M. Howell

[57] ABSTRACT

A stable lip compositions which resists transfer upon subjecting the wearer to routine or daily activities. The compositions are in the form of a lipstick, contain a sufficiently high level of silicone oils to impart good feel upon application wherein, sticks are additionally formulated to resist breakage even when exposed to the rigors of manufacture, retail sale, and daily use by the consumer.

6 Claims, No Drawings

TRANSFER-RESISTANT LIP COMPOSITIONS

CROSS REFERENCE

This application claims priority under Title 35, United States Code 119(e) from Provisional Application Ser. No. 60/009,936, filed Jan. 16, 1996 and Provisional Application Ser. No. 60/015,487, filed Apr. 15, 1996.

TECHNICAL FIELD

The present invention relates to stable lip compositions which resists transfer upon subjecting the wearer to routine or daily activities. Said compositions in the form of a lipstick, contain a sufficiently high level of silicone oils to impart good feel upon application. Said sticks are additionally formulated to resist breakage even when subjected to the rigors of manufacture, retail sale, and daily use by the consumer.

BACKGROUND OF THE INVENTION

Lip treatment products whose primary purpose is to extend wear, improve the blot transfer resistance and heighten the gloss of said lipstick are well known in the art. Some of these products such as overcoats utilize a variety of polymeric fluids and film forming technologies to form a barrier layer that avoids transference of the lipstick it is applied over. Examples of such compositions are disclosed in Japanese Patent Application Number HEI 5[1993]-221829, published Aug. 31, 1993 and copending U.S. Ser. No. 08/361,246, filed Dec. 21, 1994; both incorporated herein by reference. Although said overcoat products can be effective in preventing inadvertent transfer onto objects, they do require separate application over the pigmented lip composition applied to the lips. It is, therefore, advantageous to provide a transfer resistant product that applied in a single step.

European Patent Application 0 602 905 A2, published Jun. 22, 1994, discloses lip stick compositions comprising volatile solvents, waxes, powders oils, and a silicone resin which resists transfer without the use of an overcoat as disclosed above. These compositions, however, rely on the combination of the volatile solvent and silicone resin which is reported to mitigate the transference problems associated with conventional lipsticks.

SUMMARY OF THE INVENTION

The present invention is a lip composition applied in a single step which resists transfer. Said compositions achieve this by combining materials routinely used in the cosmetic industry. By the selection of these components in the specific levels disclosed herein, transference is minimized while the wearer goes about their daily activities including eating and drinking.

Another object of the present invention is to provide a composition having desirable application and feel characteristics as well as improve luster and shine of the composition once applied to the lips.

Still another object of the present invention is to provide a lipstick composition that resists breakage even when exposed to the rigors of manufacture, retail sale, and daily use by the consumer.

A last objective of the present invention is to provide processing steps to manufacture compositions disclosed herein.

The composition of the present invention can take a number of forms often associated with lip composition, including solid sticks, creams and balms. Unless otherwise indicated, all percentages disclosed herein are by total weight of the composition.

DETAILED DESCRIPTION OF THE INVENTION

The present composition comprises lipophilic materials selected from the group consisting of waxes, oils. These materials comprises from about 30% to about 95%, preferably from about 50% to about 85%, and most preferably from about 50% to about 60% of the composition.

Waxes act as solidifying agents thereby assisting in forming solid structures such as "bullet" shaped lipsticks. Waxes as used herein are defined as organic compounds or mixtures of high molecular weight substances, that are thermoplastic, forming a solid mass at ambient temperature/room temperature. As used herein wax refers to single type of wax or mixtures of waxes.

Said waxes include hydrocarbons or esters of fatty acids and fatty alcohols and are derived from natural, synthetic and mineral sources. Natural waxes can be of animal origin, such as beeswax, spermaceti, lanolin, shellac wax, of vegetable origin, e.g. carnauba, candelilla, bayberry, sugarcane wax, or of mineral origin, e.g. ozokerite, ceresin, montan, paraffin, microcrystalline wax, petroleum and petrolatum wax.

Synthetic waxes include those disclosed in Warth, *Chemistry and Technology of Waxes*, Part 2, 1956, Reinhold Publishing; herein incorporated by reference. The waxes most useful herein have melting points from about 55° C. to about 115° C. and are selected from the $C_8$ to $C_{50}$ hydrocarbon waxes. Such waxes include long chained polymers of ethylene oxide combined with a dihydric alcohol, namely polyoxyethylene glycol. Such waxes include carbowax available from Carbide and Carbon Chemicals company. Other synthetic waxes include long-chained polymers of ethylene with OH or other stop length grouping at end of chain. Such waxes include the Fischer-Tropsch waxes as disclosed in the text disclosed above at pages 465–469 and include Rosswax, available from Ross company and PT-0602 available from Astor Wax Company.

The waxes preferred for use in the present compositions are selected from the group consisting of candelilla, beeswax, beeswax having free fatty acids removed (modified beeswax), carnauba, spermaceti, montan, ozokerite, ceresin, paraffin, bayberry, castor waxes, synthetic waxes, microcrystalline waxes, silicone waxes (modified to be compatible with other first materials) and mixtures thereof. More preferably the waxes are selected from the group consisting of microcrystalline, spermaceti, candelilla, modified beeswax, carnauba, ozokerite, paraffin, ceresin, silicone waxes, Fischer-Tropsch waxes, Carbowaxes and mixtures thereof. Most preferably, the waxes are selected from the group consisting of candelilla, ozokerite, paraffin, carnanuba wax, Fischer-Tropsch waxes and mixtures thereof.

Oils used in the present invention have a number of functional purposes, for example application, adhesion, gloss and perhaps most importantly occlusive moisturization. Said oils include organic substances that are liquid at ambient temperature and include esters, triglycerides, hydrocarbons, silicones and mixtures thereof. Specific oils useful in the present invention include caprylic triglycerides; capric triglycerides; isostearic triglycerides; adipic triglycerides; wheat germ oil; hydrogenated vegetable oils; petrolatum; branched-chain hydrocarbons; alcohols and esters; castor oil; lanolin oil; corn oil; cottonseed oil; olive oil; palm kernel oil; rapeseed oil; safflower oil; jojoba oil; evening primrose oil; avocado oil; mineral oil; sheabutter; octylpalmitate; maleated soybean oil; glycerol trioctanoate; diisopropyl dimerate; isocetyl citrate; volatile and non-volatile silicone oils including dimethicone, phenyl dimethicone, cyclomethicone, poly(perfluoroalkyl) siloxanes, linear and cyclic polyalkyl siloxanes and mixtures thereof. Preferable oils used in the present invention are selected from the group consisting of caprylic triglycerides, capric triglycerides, isostearic triglyceride, castor oil, adipic triglyceride, diisopropyl dimerate, dimethicone, octyl dodecanol, oleyl alcohol, hydrogenated vegetable oils, maleated soybean oil, lanolin oil, polybutene, oleyl alcohol; hexadecyl alcohol wheat germ glycerides and mixtures thereof. The individual oils or the aggregate of the oils selected should be soluble with the liquefied waxes selected for use herein. Therefore, oils have a solubility parameter from about 5 to about 10. The respective solubility parameters for waxes and oils are reported in "Cosmetics & Toiletries", Vol 103, October 1988; incorporated herein by reference.

Oils useful in present invention include emollients, humectants, occlusives and mixtures thereof. Emollients useful in the present invention are found in The C.T.F.A. Cosmetic Ingredient Handbook, pages 572–575, 1992; herein incorporated by reference. Said emollients include lanolin, synthetic lanolin derivatives, modified lanolins, isopropyl palmitate, isononyl isononanoate, isopropyl isostearate, cetyl ricinoleate, octyl palmitate, cetyl ricinoleate, glyceryl trioctanoate, diisopropyl dimerate, propylene glycol, polyglycerol esters, myristyl acetate, isopropyl myristate, diethyl sebacate; diisopropyl adipate; tocopheryl acetate; tocopheryl linoleate; hexadecyl stearate; ethyl lactate; cetyl lactate, cetyl oleate, octyl hydroxystearate; octyl dodecanol, decyl oleate, propylene glycol ricinoleate, isopropyl lanolate, pentaerythrityl tetrastearate, neopentylglycol dicaprylate/dicaprate, hydrogenated cocoglycerides, isotridecyl isononanoate, isononyl isononanoate, myristal myristate, triisocetyl citrate, cetyl alcohol, octyl dodecanol, oleyl alcohol and mixtures therefor. Particularly useful emollients are selected from the group consisting of lanolin, diisopropyl dimerate, polyglycerol esters, isopropyl isostearate, cetyl lactate, octyl hydroxystearate and mixtures thereof.

Humectants useful in the present invention include those as disclosed in The C.T.F.A. Cosmetic Ingredient Handbook, page 567, 1992; herein incorporated by reference. Occulsives useful in the present invention are likewise found in the C.T.F.A. Cosmetic Ingredient Handbook, at pages 578–580; herein incorporated by reference.

Other oils useful in the present invention include volatile fluids. These fluids improve the ease of application of the composition over the lips. As the volatile fluid escapes from the composition after application, the composition's viscosity increases rapidly, imparting a pleasant, lubricious feel to the lips. Said volatile fluids are selected from the group consisting of volatile hydrocarbons, volatile silicones and mixtures thereof. Compositions of the present invention may comprise from about 1% to 70%, preferably 10% to 60%, and most preferably from 20% to 50% volatile fluids. Preferred volatile hydrocarbons fluids include isododecane, available as for example Permethyl 99A from Permethyl Corporation corresponding to the formula:

$$CH_3(CH_2)_{10}CH_3$$

Preferred volatile silicone fluids include cyclomethicones having 3, 4 and 5 membered ring structures corresponding to the formula:

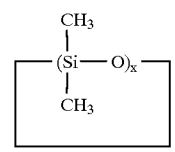

where X is from about 3 to about 6. Said volatile silicones include 244 Fluid, 344 Fluid and 345 Fluid from Dow Corning Corporation.

Other silicone fluids useful in the present invention include poly(organosiloxane) fluids conforming to the formula:

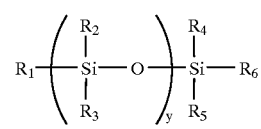

wherein the end groups $R_1$ and $R_6$ are independently selected from the group consisting of hydroxyl groups, lower alkyl groups having carbon chain lengths from about $C_1$ to about $C_6$ and mixtures thereof, preferably methyl groups and the non-end groups $R_2$, $R_3$, $R_4$ and $R_5$ are independently selected from methyl groups, fluoroalkyl groups, phenyl groups and mixtures thereof.

The poly(organosiloxane) fluids with non-end groups ($R_2$, $R_3$, $R_4$ and $R_5$) comprising methyl groups are known in the art and provide the final product with a relatively non-lipohilic character. Commercially available non-volatile silicone fluids having such non-end groups include those available from Dow Corning as the 200 Fluids, and those available from General Electric as SF-96 Series.

Silicone fluids with non-end groups comprising fluoroalkyl groups are also useful herein. It is preferable, however, that the fluorine atom is attached to alkyl groups having a $C_3$ to $C_8$ chain length wherein the fluorine atom is attached to attached to said alkyl group at a point no closer than third carbon atoms from the silicone/carbon bond. Commercially available non-volatile silicone fluids having such non-end groups include those available from Dow Corning as the 1265 Fluid series, and those available from General Electric as the SF-1153 Series, most preferred is the 1265 Fluid Series, most preferably those of having a viscosity from about 100 cSt to about 350 cSt.

Silicone fluids with the non-end groups comprising allyl groups are also useful in the present invention. The allyl groups which are particularly useful in the present invention are phenyl groups. Particularly useful allyl-substituted silicone fluids commercially available are available as the 556 Series from Dow Corning.

Preferable poly(organosiloxane) fluids of the present invention are selected from the group consisting of poly (dimethylsiloxane) fluids, poly(phenylmethylsiloxane) fluids, poly(fluoroalkylmethylsiloxane) fluids, the copolymers of said fluids and mixtures thereof. More preferred fluids are selected from the group consisting of poly (dimethylsiloxane) fluids, their copolymers and mixtures thereof. Most preferred are poly(dimethylsiloxane) fluids and their copolymers, preferably selected from the group consisting of dimethicone, phenyl dimethicone, phenyl trimethicone and mixtures thereof.

Non-silicone fluids also useful as a second material of the present invention include perfluoropolyethers of general formula:

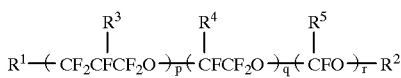

wherein $R^1$ though $R^5$ are selected from the group consisting of fluorine atoms, perfluoroalkyl groups, oxyperfluoroalkyl groups and mixtures thereof, the value of p, q, and r collectively are of a value such that the perfluoropolyether molecular weight is from about 500 to about 10,000 wherein p, q and r may be equal. A preferred perfluoropolyether is the commercially available product known as Fomblin HC-01, -02, -03 and -04, HC-25 and HC-R available from Montefluosu of Milano, Italy. Non-volatile perfluoropolyethers are preferred.

C. Optional Ingredients

Compositions of the present invention further include optional ingredients which may be added to the composition disclosed above to provide various consumer desirable characteristics to the product. Said optional ingredients include those routinely used in the cosmetic arts to produce a specific cosmetic effect which is deemed desirable.

Surfactants may be used in the present invention insofar as they do not sufficiently stabilize the second material dispersed within the first material or allowing said second material to coalescence upon application to the lips. Surfactants are well known to those skilled in the art of lipstick making in order to enhance dispersability of pigments and other solid materials like mica and talc, stabilize liquid dispersed phases such as water, glycerine and glycols, provide skin benefits such as emolliency, and skin feel modifiers; i.e. the right combination can make the stick less hard. Anionic surfactants, nonionic surfactants, cationic surfactants, amphoteric surfactants and mixtures thereof are suitable for use. The more common surfactants used in the present invention include those found in the C.T.F.A. Cosmetic Ingredient Handbook, pages 587–592, 1992; herein incorporated by reference. Some of the more commonly used ones include ethoxylated castor oil, lecithin, fatty acids and salts of fatty acids (sodium stearate, stearic acid, oleic acid, potassium stearate, zinc stearate), fatty alcohols (oleyl alcohol, e.g.), ascorbyl palmitate, oxidized waxes, mono and diglycerides(glyceryl oleate), lauroyl lysine, cetyl lactate and mixtures thereof.

In addition to surfactants other ingredients such as preservatives, sunscreens, UV absorbers, anti-oxidants, flavorings, perfumes, colorants, dyes and other ingredients routinely used in the art. In the case of dyes and colorants which are incorporated into the first material, it is important that the first and second materials are sufficiently incompatible to avoid tinting or coloring the second material.

EXAMPLES

| Ingredient | Weight Percent (%) |
|---|---|
| Example 1: | |
| Synthetic Wax[1] | 9.4 |
| Ozokerite | 3.0 |
| Paraffin | 7.6 |
| Diisostearate Dimerate | 16.7 |
| Polyglycerol - 3 Diisostearate | 3.0 |
| Propyl Paraben | 0.1 |
| Mixed Tocopherol | 0.2 |
| Pigments/Pearls | 12.5 |
| Cyclomethicone[2] | 17.5 |
| Cyclomethicone[3] | 25.0 |
| Isoparaffin[4] | 5.0 |

1. available from Astor Wax as PT-0602.
2. available from Dow Corning as Dow 244.
3. available from Dow Corning as Dow 345.
4. available from the Permethyl Company as Permethyl 99A.

| Example 2: | |
|---|---|
| Synthetic Wax[1] | 11.0 |
| Ozokerite | 3.0 |
| Paraffin | 5.0 |
| Diisostearate Dimerate | 17.7 |
| Polyglycerol - 3 Diisostearate | 3.0 |
| Propyl Paraben | 0.1 |
| Mixed Tocopherol | 0.2 |
| Pigments/Pearls | 12.5 |
| Cyclomethicone[2] | 6.5 |
| Cyclomethicone[3] | 30.0 |
| Isoparaffin[4] | 11.0 |

1. available from Astor Wax as PT-0602.
2. available from Dow Corning as Dow 244.
3. available from Dow Corning as Dow 345.
4. available from the Permethyl Company as Permethyl 99A.

| Example 3: | |
|---|---|
| Synthetic Wax[1] | 5.0 |
| Ozokerite | 14.0 |
| Diisostearate Dimerate | 17.7 |
| Polyglycerol - 3 Diisostearate | 3.0 |
| Propyl Paraben | 0.1 |
| Mixed Tocopherol | 0.2 |
| Pigments/Pearls | 10.0 |
| Cyclomethicone[2] | 3.0 |
| Cyclomethicone[3] | 35.0 |
| Isoparaffin[4] | 12.0 |

1. available from Ross Company as Rosswax 100.
2. available from Dow Corning as Dow 244.
3. available from Dow Corning as Dow 345.
4. available from the Permethyl Company as Permethyl 99A.

| Example 4: | |
|---|---|
| Synthetic Wax[1] | 4.0 |
| Ozokerite | 14.0 |

-continued

| Ingredient | Weight Percent (%) |
| --- | --- |
| Diisostearate Dimerate | 19.2 |
| Polyglycerol - 3 Diisostearate | 3.0 |
| Propyl Paraben | 0.1 |
| Mixed Tocopherol | 0.2 |
| Pigments/Pearls | 12.0 |
| Cyclomethicone[2] | 6.0 |
| Cyclomethicone[3] | 35.0 |
| Isoparaffin[4] | 6.5 |

1. available from Ross Company as Rosswax 100.
2. available from Dow Corning as Dow 244.
3. available from Dow Corning as Dow 345.
4. available from the Permethyl Company as Permethyl 99A.

Example 5:

| | |
| --- | --- |
| Synthetic Wax[1] | 4.0 |
| Ozokerite | 14.0 |
| Paraffin Wax | 2.0 |
| Triisocetyl Citrate | 19.1 |
| Propyl Paraben | 0.1 |
| Mixed Tocopherol | 0.2 |
| Pigments/Pearls | 10.1 |
| Cyclomethicone[2] | 25.5 |
| Cyclomethicone[3] | 20.0 |
| Isoparaffin[4] | 5.0 |

1. available from Ross Company as Rosswax 100.
2. available from Dow Corning as Dow 244.
3. available from Dow Corning as Dow 345.
4. available from the Permethyl Company as Permethyl 99A.

Example 6:

| | |
| --- | --- |
| Synthetic Wax[1] | 11.0 |
| Ozokerite | 3.0 |
| Paraffin | 5.0 |
| Diisopropyl Dimer Dilinoleate | 17.7 |
| Polyglycerol - 3 Diisostearate | 3.0 |
| Propyl Paraben | 0.1 |
| Tocopherol | 0.2 |
| Pigments/Pearls | 9.7 |
| Stainer | 0.3 |
| Cyclomethicone[2] | 6.5 |
| Cyclomethicone[3] | 35.0 |
| Isoparaffin[4] | 8.5 |

1. available from Astor Wax as PT-0602.
2. available from Dow Corning as Dow 244.
3. available from Dow Corning as Dow 345.
4. available from the Permethyl Company as Permethyl 99A.

METHOD OF MANUFACTURE

Examples 1–5 are assembled according to the following instructions:

Combine the pigments and a sufficient amount of the primary liquid emollient (diisopropyl dimerate, triisocetyl citrate etc.) in a vessel with stirring until the pigments are fully incorporated into the liquid (usually about a 40% pigment/60% liquid mixture). Pass the mixture through a 3-roll mill three times yielding a dispersion of pigment particles in oil; hereinafter referred to as the slurry.

Combine all non-volatile ingredients (waxes, oils, slurry, pearls, preservatives etc.) in a sealed vessel equipped with heating and mixing. With continuous mixing, heat the combination until all waxes are completely melted (between 90 and 115° C.). While maintaining the temperature, stir the combination of ingredients for about 30 minutes.

Add the volatile liquids (cyclomethicone and isoparaffin) into the melted wax/oil/pigment mixture. Quickly seal the vessel, resume agitation and return the mixture to the full melt temperature. Once melt temperature is reached stir mixture for approximately an additional 10 minutes. Pour the combination immediately into a room temperature aluminum bullet mold. Cool the filled mold either in a freezer or on a chill table until the combination is solid. Remove the solid composition from the molds and place in suitable cosmetic packaging.

What is claimed is:

1. A transfer resistant lipstick comprising:
   a. from 4% to 11% synthetic wax;
   b. from 3% to 14% ozokerite wax;
   c. from 0% to 7.6% paraffin wax;
   d. from 36.5% to 45.5% cyclomethicone;
   e. from 5% to 12% volatile isoparaffin;
   f. a material selected from the group consisting of diisostearate dimerate, triisocetyl citrate or diisopropyl dimer dilinoleate; and
   g. from 9.7% to 12.5% of a coloring agent selected from the group consisting of pigments, pearls and mixtures thereof.

2. A lipstick composition according to claim 1 which comprises from 0% to 3% polyglycerol-3 diisostearate.

3. A lipstick composition according to claim 2 which comprises from 0% to 0.3% stainers.

4. A lipstick composition according to claim 3 which comprises from 0% to 0.2% mixed tocopherol.

5. A lipstick composition according to claim 1, comprising from 2% to 7.6% paraffin wax.

6. A lipstick composition according to claim 1, comprising from 2% to 5% paraffin wax.

* * * * *